United States Patent [19]

Cude

[11] Patent Number: 5,065,296
[45] Date of Patent: Nov. 12, 1991

[54] HANDLE AND COVER FOR POSITIONABLE LIGHTING FIXTURE

[75] Inventor: John M. Cude, Portland, Tenn.

[73] Assignee: DeRoyal Industries, Inc., Powell, Tenn.

[21] Appl. No.: 672,379

[22] Filed: Mar. 20, 1991

[51] Int. Cl.5 ............................................. F21L 15/12
[52] U.S. Cl. ..................................... 362/399; 362/804
[58] Field of Search ................................. 362/804, 399

[56] References Cited

U.S. PATENT DOCUMENTS

| | | | |
|---|---|---|---|
| 4,559,671 | 12/1985 | Andrews et al. | 362/804 |
| 4,605,124 | 8/1986 | Sandel et al. | 362/399 |
| 4,844,252 | 7/1989 | Barron et al. | 362/804 |
| 4,878,156 | 10/1989 | Hallings et al. | 362/399 |
| 4,976,299 | 12/1990 | Bickelman | 362/804 |

*Primary Examiner*—Carroll B. Dority
*Attorney, Agent, or Firm*—Luedeka, Hodges, Neely & Graham

[57] ABSTRACT

A handle and cooperating cover for a moveable lighting fixture, particularly a lighting fixture of the type utilized in surgical operating rooms or like environments. The handle is provided with an elongated body that is attachable at one end thereof to the light fixture and includes a circular shoulder radially projecting from the elongated body near the end thereof that is attached to the light fixture. The cover comprises an elongated hollow tubular section having a closed end and an open end and which fits over the elongated body of the handle and includes a radially extending flange section adjacent the open end of the tubular section. Latch means are carried by the flange section for engaging lip means defined by the radial edge region of the circular shoulder to removably secure the cover in position on the handle.

17 Claims, 3 Drawing Sheets

HANDLE AND COVER FOR POSITIONABLE LIGHTING FIXTURE

BACKGROUND OF THE INVENTION

The present invention relates generally to a replaceable cover for a handle utilized for manipulating or adjusting the position of a mechanism employable in a sterile environment, and more particularly to a disposable cover and handle to be covered thereby that is attachable to a light fixture employed in surgical operating rooms and like environments and selectively positioned by the manipulation of the handle.

Much of the equipment used in clean or sterile environments such as in surgical operating rooms has to be physically handled by personnel after they have scrubbed, donned sterile clothing, gloves, and otherwise rendered free of contaminants. One such piece of equipment which is routinely used in surgical operating rooms and handled by the surgeon and the attendants thereto at times immediately proceeding and during any given surgical procedure is a position-adjustable light fixture which is usually mounted above the operating table and used for projecting a concentrated high-intensity beam of light onto the patient undergoing the operation. The light fixture is positionable to concentrate the light beam onto a particular portion of the patient's anatomy or to vary the light intensity by moving the light fixture closer to or further away from the patient. This maneuvering of the light fixture is normally accomplished by grasping a handle projecting from the light fixture and then selectively positioning the light fixture through an adjustable light support to provide the desired light orientation and/or light intensity. This handle is usually attached to the underside or base of the light fixture at a central location and is of a considerable concern with respect to maintaining the desired level of sterility or cleanliness in the operating theater due to the frequent contacting of the handle by the surgical personnel.

Efforts to overcome this problem so as to assure that the handle of the positionable light fixture is not a source of possible contamination in the operating room include the use of disposable covers on the light handle. For example, U.S. Pat. No. 4,605,124 is directed to several embodiments of sterilizable covers designed for use on handles projecting from adjustable light fixtures as utilized in surgical operating rooms. While such covers for light fixture handles have helped reduce contamination problems encountered in surgical operating rooms, there are several shortcomings or drawbacks attendant with these previously known covers which detract from their overall desirability and usefulness. For example, the covers described in the aforementioned patent have handle-receiving grip portions which depend upon friction or the like to ensure retention of the cover on the light handle. In the aforementioned patent it is suggested that adhesive means can be used on a flange integral with the grip portion at a location between the cover and the light fixture to further the attachment between the cover and the handle. Another previously known cover utilizes a finger-forming serrated flap about the opening of a cover portion designed to fit over the grip portion of the light fixture handle. The radially extending fingers of the serrated flap bear against the handle to frictionally hold the cover on the handle.

With these previously known covers it is difficult to maintain sterile conditions in the operating arena when attaching the cover to the handle of the light fixture prior to or during the operating procedure by a surgeon or attendant thereto. For instance, when using previously known covers, it was found necessary for the surgeon or an attendant to grasp the light fixture with one hand to hold the light fixture in place while applying sufficient force on the cover with the other hand for forcing the cover onto. This required grasping of the light fixture represents a significant source of contamination.

SUMMARY OF THE INVENTION

It is, therefore, an object of the present invention to obviate or substantially minimize the above and other shortcomings or drawbacks attendant with the use of the aforementioned and previously known covers used for covering handles on position-adjustable light fixtures by providing a relatively easily attachable and detachable sterile cover for covering a particularly configured handle securable to such a light fixture.

Another object of the present invention is to provide a cover for a handle on a position-adjustable surgical light fixture with a simple yet positive latch mechanism which provides for the attaching of the cover to the handle in such a manner that the cover can be readily placed over the handle and securely attached thereto by employing only a single hand and without requiring the surgeon or his assistant to directly contacting the handle or any other surface of the light fixture.

A further object of the present invention is to provide a cover with a latch mechanism which permits the removal of the cover from the handle by the light fixture by simply engaging a portion of the cover for moving the latch mechanism out of engagement with the handle so that the cover can be readily slipped off of the handle.

A still further object of the present invention is to provide a handle which is constructed to be engaged by the latch mechanism carried by the cover for releasably securing the cover onto the handle assembly.

A still further object of the present invention is to provide a plurality of handle assemblies each usable with the cover of the present invention but differing from one another by the means used to attach the handle to the light fixture.

A still further object of the present invention is to provide a handle and cover assembly to be used jointly with position-adjustable light fixtures of the type utilized in surgical operating rooms.

Generally, in a lighting fixture which is movable by means of an elongated handle projecting therefrom, the improvement of the present invention comprises a substantially rigid circumferential shoulder disposed on and generally radially projecting from the handle at a location adjacent to the lighting fixture. The cover means for the handle comprise an elongated tubular portion which is closed at one end and open at its opposite end to define a perimeter. The cover means has circumferential flange means projecting generally radially outwardly from the perimeter at the open end of the elongated tubular portion. Latch means are carried by the flange means at a location thereon whereby the latch means is in position to engage lip means defined on the shoulder when the tubular portion of the cover means is received by the elongated handle and the latch means are urged toward the circumferential shoulder.

In one embodiment, the circumferential flange is resilient so that the latch means can be displaced radially as the cover means is being placed on the handle to urge the latch means into engagement with the lip means defined on the circumferential shoulder and effect the rebounding of the latch means to maintain its engagement with the lip means.

The elongated body of the handle means is provided with suitable means at the end thereof near the circumferential shoulder for attaching the handle means to the light fixture.

Other and further objects of the present invention will become obvious upon an understanding of the illustrative embodiments about to be described or will be indicated in the appended claims, and various advantages not referred to herein will occur to one skilled in the art upon employment of the invention in practice.

Preferred embodiments of the invention have been chosen for the purpose of illustration and description. The preferred embodiments illustrated are not intended to be exhaustive nor to limit the invention to the precise forms shown. The preferred embodiments are chosen and described in order to best explain the principles of the invention and their application and practical use to thereby enable others skilled in the art to best utilize the invention in various embodiments and modifications as are best adapted to the particular use contemplated.

DETAILED DESCRIPTION OF THE PRESENT INVENTION

Figure 1:
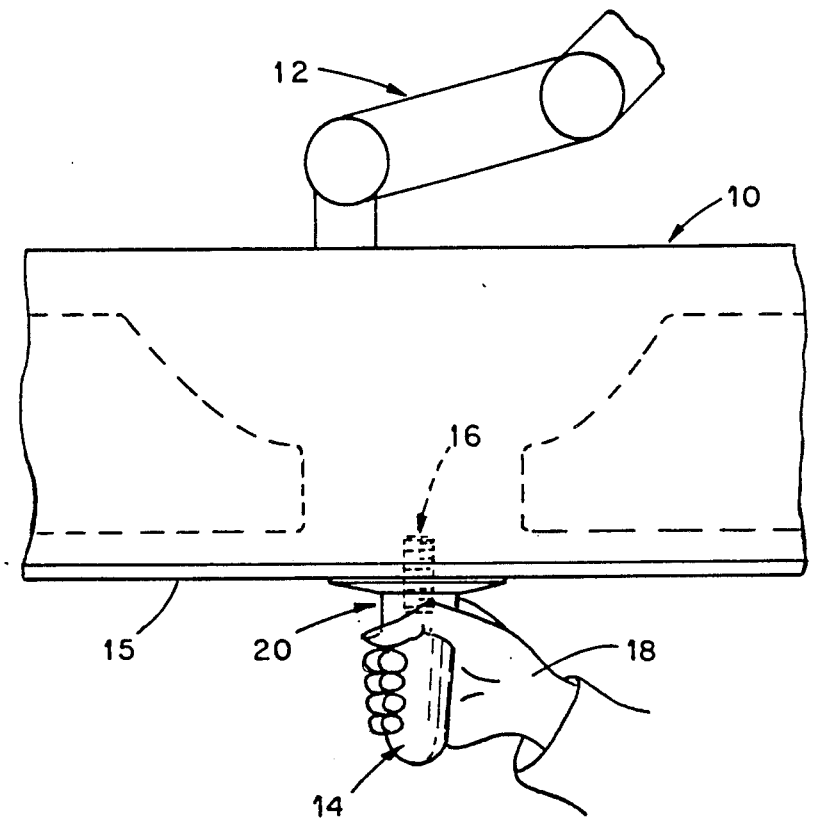
FIG. 1 is a elevational view generally illustrating a selectively-positionable light fixture, partially broken away, with a position-adjustable handle and cover thereon embodying various features of the present invention.

FIG. 1 generally illustrates a light fixture 10 which is representative of the type of light fixture conventionally utilized in surgical operating rooms and which is selectively positionable by mounting the light fixture on position-adjustable mechanisms such as a mounting having articulated segments as generally shown at 12. The positioning of the light fixture 10 for providing the desired intensity as well as the appropriate orientation of the light beam emanating from the light fixture is provided for means of a handle 14 projecting from the light fixture 10. The handle 14 is commonly removably attached to the light fixture at a central location on the base 15 of the light fixture 10. Removable attachment of the handle 14 is usually achieved by means of a threaded receptacle or boss, such as generally shown at 16, on the base 15. The selective positioning of the light fixture 10 is accomplished by the surgeon or other members of the surgical team by grasping the handle 14 with a single hand as generally shown at 18 and then positioning the light fixture 10 through the action of the mounting 12.

In accordance with the present invention the handle 14 is provided with the disposable cover 20 which is formed of a sterile or sterilizable, impervious material as will be described in detail below. The cover 20 of the present invention is readily placed onto and fixedly attached to the handle 14 with a simple one-hand movement. This simple movement of the cover onto the handle provides for snapping a latch mechanism carried by the cover 20 onto a portion of the handle 14 for securing the cover 20 onto the handle 14 so that the desired positioning of light fixture 10 may be appropriately achieved.

As best shown in FIGS. 2-5, the cover 20 of the cover-handle assembly of the present invention is provided with a hollow elongated tubular portion 22, preferably of a tapered or conical configuration and having a textured, i.e., roughened, outer grip surface thereon. The cross section within the hollow tubular portion 22 is slightly greater over the length thereof, i.e., about 0.0001 to 0.010 inch greater than contiguous portions of the cross section of the grip portion 24 of the handle 14 when the cover 20 is attached to the handle 14 so as to facilitate the placement of the cover 20 onto the handle 14. The tubular portion 22 is provided with an end wall 26 closing the end of the tubular portion 22 remote to or distal to the light fixture 10. An opening 28 into the hollow tubular portion 22 at the proximal end thereof defines a perimeter 23 on the tubular portion 22 and is of a sufficient size so that the grip portion 24 of the handle 14 may be readily received within the tubular portion 22.

Figure 2:
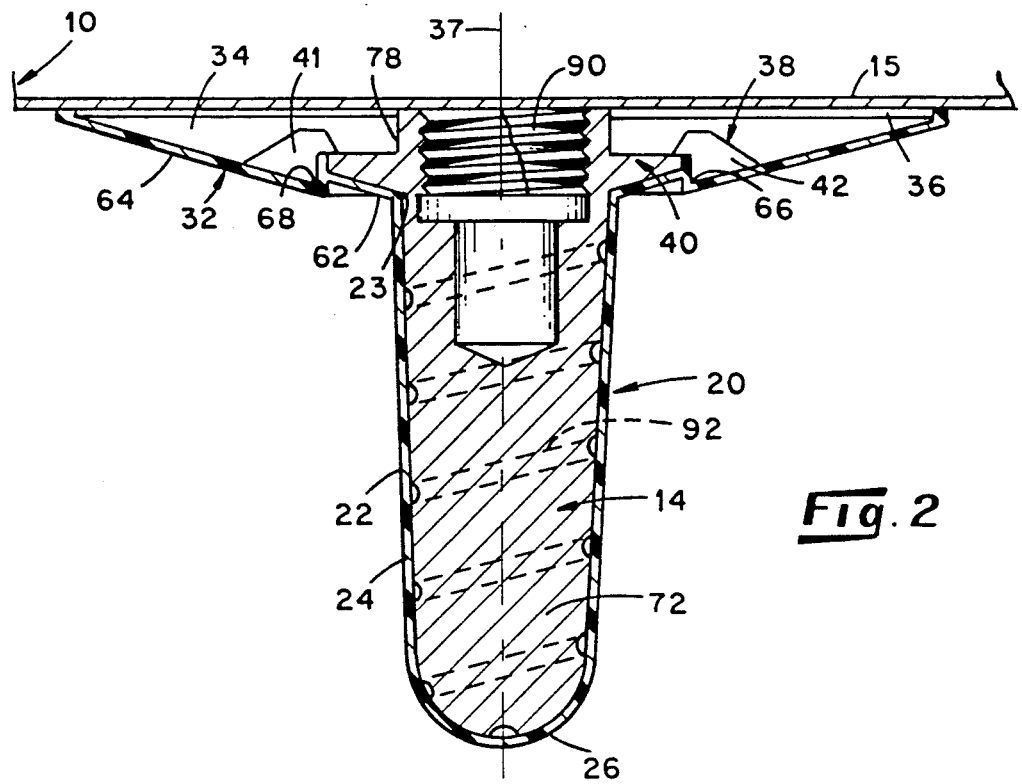
FIG. 2 is a sectional elevational view showing details of a handle and handle cover embodying various features of the present invention with the cover latched onto the handle.
Figure 3:
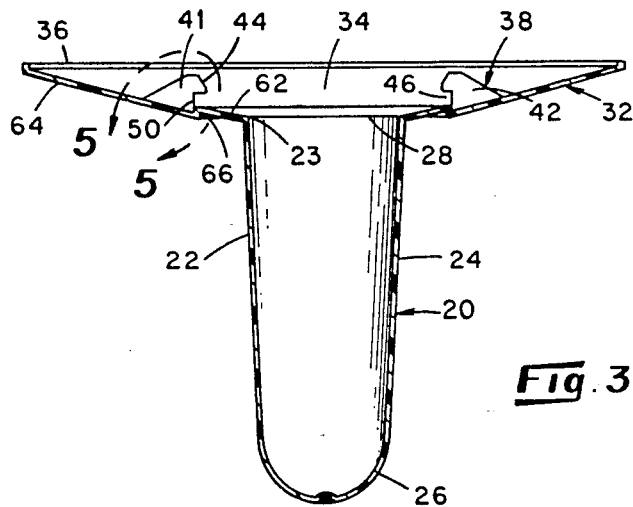
FIG. 3 is a sectional elevational view of a cover and latch mechanism carried thereby for securing the cover to a handle projecting from the base of the light fixture.

The cover 20 is provided with a flange 32 which is integral with the tubular portion 22 and disposed at the end of the tubular portion 22 near, and preferably contiguous to, the perimeter of the tubular section defined by opening 28. As best shown in FIGS. 2 and 3, the flange 32 extends generally radially outwardly from the tubular portion 22 and is of a generally dish-shaped or concave configuration with a cavity 34 formed therein facing the base 15 of the light fixture 10 when the cover 20 is attached to the handle 14. The flange 32 is preferably of a circular configuration and is preferably provided with an upright rim 36 disposed about the periphery thereof for increasing the structural integrity of the flange 32.

In accordance with the present invention, it is preferred to have the uppermost edge of the flange 32 as defined by the top of the rim 36 in a horizontal plane essentially common with the horizontal plane provided by the top or the uppermost end of the handle 14 when the cover 20 is in place thereon, as generally shown in FIG. 2. However, it will appear clear that the present invention also includes embodiments thereof wherein the rim 36 on the cover 20 may be spaced from the base 15 when the cover 20 is in place on the handle. The flange 32 of the cover 20 is of a diameter in the range of about 4 to 7 inches, preferably about 5-6 inches, which is adequate to assure that the hand of the surgeon or an attendant thereto does not contact the base 15 of the light fixture 10 while manipulating the light fixture 10. With a flange 32 of a size in this range of diameters, the angle of the dish-shaped section with respect to the longitudinal axis 37 of the handle 14 is in the range of about 10° to 30° in order to provide the cavity 34 with a sufficient depth to house the latch mechanism when the rim 36 abuts against the base 15 of the light fixture 10.

Figure 4:
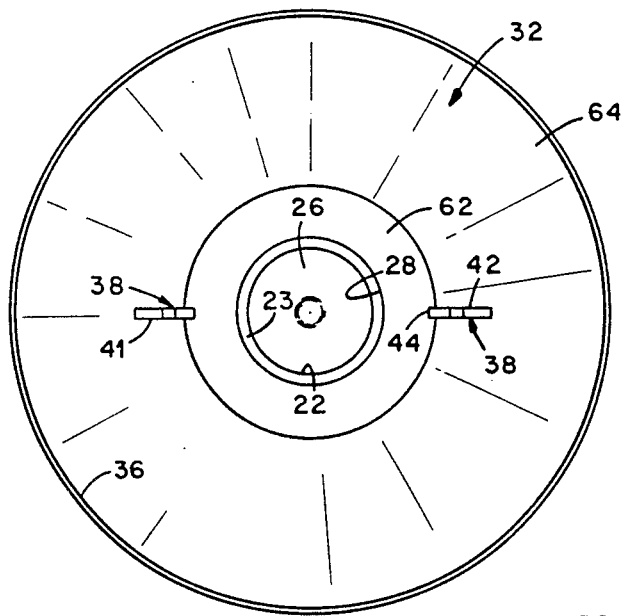
FIG. 4 is a plan view of FIG. 3 showing an embodiment of a cover which has two diametrically separated latch mechanisms supported thereby for attaching the cover to the handle.
Figure 5:
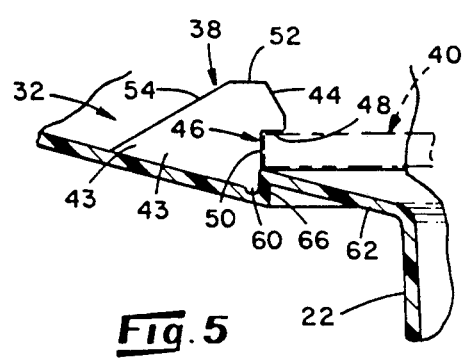
FIG. 5 is an enlarged sectional view taken along lines 5—5 of FIG. 3 and illustrating further details of the latch mechanism and one embodiment of hinge arrangement utilized for facilitating the engagement and disengagement the cover of the latch mechanism with the handle.

The latch mechanism for releasable securing the cover 20 to the handle 14 when attached to the base 15 of the light fixture 10 is provided by latch means 38 which engage end portions defining lip means on a shoulder 40 radially extending from the handle 14 near the top end thereof and into cavity 34 when the cover 20 is in place on the handle 14. The latch means 38 is radially displaced or pivotally actuated by the shoulder 40 upon contact therewith during the placement of the cover 20 over the handle so as to first urge the latch means 38 out of the way of the shoulder 40 for permitting passage of the shoulder 40 over a portion of the latch means 38 and into a shoulder retaining or engaging portion of the latch means 38. The latch means then rebounds to maintain the retention of the lip means in the flange retaining portion of the latch means. As best shown in FIGS. 3-5, the latch means 38 is provided by two similarly constructed latches 41 and 42 which are circumferentially, preferably diametrically, spaced from one another about the cavity 34 at a radial location on the flange 32 uniformly spaced from the longitudinal axis 37 of the handle 14 and intermediate the tubular portion 22 and the rim 36. Each of these latches 41 and 42 is shown provided by an elongated upright projection or lug 43 having parallel side walls radially oriented in the cavity 34. Each latch 41 or 42 is provided with an inner wall 44 which extends between the side walls and faces generally inwardly towards the opening 28 in the cover 20. A notch or detent 46 in end wall 44 is utilized to engage lip means on the shoulder 40 to secure the cover 20 onto the handle 14. This notch 46 is of a sufficient size within the latch body 43 to receive and contact a sufficient radial edge region of the shoulder 40 for retaining the cover 20 on the handle 14. The notch 46 faces the opening 28 in the cover and is preferably in the form of a right angle so as to have an upper surface 48 oriented in a plane parallel with the upper surface of the shoulder 40 and a rear wall 50 perpendicular to the notch surface 48. The notch surface 48 is preferably about 0.05 to 0.125 inch in length so as to contact a sufficient surface portion of the shoulder 40 to hold the cover 20 in place and yet provide adequate displacement of the latches to permit the engagement or disengagement of the latches with the shoulder 40. The rear wall 50 of the notch 46 is preferably radially offset from the longitudinal axis 37 of the handle 14 a distance slightly less, i.e., about 0.001 to 0.010 inch, than the radius of the shoulder 40 so that when the latch means 38 engages the shoulder 40 sufficient contact of shoulder 40 with the surfaces defining the notch 46 including the rear wall 50 thereof is achieved for retaining the cover 20 on the handle 14 with minimal slippage.

In order to adequately displace the latch body 43 away from the shoulder 40 during the insertion of the cover 20 onto the handle 14 by the contact between the leading or outermost surface of the shoulder 40 and the end wall 44, the end wall 44 of the latch body 43 is preferably inclined at an angle to the longitudinal axis 37 which will permit sufficient radial displacement or the pivoting of the body 43 away from the shoulder 40 for effecting the reception of the shoulder 40 within the notch 46. The uppermost end of the end wall 44, as generally indicated at 52, is located radially outwardly from the outermost edge of the shoulder 40 so that when the shoulder 40 comes into contact with the latch 41 and 42 it engages the angled wall 44 thereon. This wall 44 may be inclined at any angle which is sufficient to provide the required radial displacement, tilting, or pivoting of the latch means 38. Satisfactory results can be achieved by using a wall angle which is preferably in the range of about 10° to 60°, more preferably about 20° to 50°, and most preferably 30°.

The body 43 of the latches 41 and 42 is formed integrally with the flange 32 and is of sufficient structural integrity so as to sufficiently retain its shape after the shoulder 40 is engaged in the notch 46 so as to secure the cover 20 to the handle 14. The radially extending latch body 43 may be of any suitable length in the range of about 0.25 to 0.75 inch and be of a thickness between the parallel side walls in the range of about 0.030 to about 0.10 inch, more preferably in the range of about 0.060 to 0.010 inch, and most preferably to about 0.080 of an inch when formed of a material suitable for the fabrication of the cover as will be described below. The rear wall 54 of the latch body 43, which extends from the top or uppermost end 52 of the latch body 43 to the surface of the flange 32, may be inclined at any angle suitable to provide the latch body with the desired length.

In order for the radial displacement of the diametrically opposed latches 41 and 42 to occur for latching the cover 20 onto the handle 14, at least a portion of the flange 32 is rendered sufficiently flexible or resilient to provide for the shoulder-receiving movement of the latch body 43. To provide the flange 32 with such resiliency, the flange 32 is formed of an integral stepped construction defined by a first circular or annular segment 62 disposed between the elongated tubular portion 22 of the cover 20 and the rear wall 50 of the notch 46. A second annular segment 64 is disposed radially outwardly from the first segment 62 with the radially innermost edge thereof being located in a plane generally underlying the outermost edge of segment 62. The segments 62 and 64 are interconnected by a riser 66 which underlies the vertically extending rear wall 50 of the notch 46. Preferably, the riser 66 is inclined away the tubular portion 22 at an angle of about 3° to 7° from the longitudinal axis 37 so as to facilitate the pivoting motion of the latch means 38 about a pivot point provided primarily in the region of the juncture between the segment 64 and the riser 66. The latches 41 and 42 are disposed on the upper surface of second segment 64.

The hinging action provided by the presence of the stepped segments 62 and 64 is further improved by providing the segment 64 with a circumferential recess 68 at a point contiguous to the juncture of the segment 68 with the riser 66. This recess 68 provides an integral hinge mechanism defined by a structurally weakened portion of the flange 32 so as to further facilitate the bending of the flange 32 at the pivot point. This annular recess 68 extends through the wall thickness of the segment a distance sufficient to substantially increase the level of flexibility of the flange 32 while assuring that the flange 32 retains sufficient strength to assure the structural integrity of the flange 32 during the attachment and the detachment of the cover 20 from the handle 14. The recess 68 may extend into the segment 64 of the flange 32 from either side thereof (shown on the side of the cavity 34), is preferably substantially U-shaped, and preferably extends into the segment 64 to a depth corresponding to about one-tenth to about one-half of the wall thickness of the segment 64.

In accordance with the present invention, hinge means for facilitating the radial displacement of the latch means 38 may be provided by either the stepped construction of the flange 32 or the circumferential recess 68. Preferably, the stepped construction and the circumferential recess are used together to assure the use of minimal effort for attaching or detaching the cover 20 from the handle.

As briefly mentioned above, the cover 20 may be formed of any suitable resilient material which is sterile or sterilizable and which possesses sufficient structural integrity and imperviousness to provide the function desired of the cover 20. The materials which may be used for the cover 20 are those which may be formed into the desired shape of the cover 20 by employing any suitable shape-forming technique such as provided by molding, casting, and the like. Suitable materials include various thermosetting or thermoplastic polymers such as polyethylene, polyurethanes, silicone, nylon, and the like. These materials are relatively impervious, possess sufficient structural integrity so as to provide for the construction of the cover 20 with relatively thin walls, and can be adequately sterilized for use in surgical operating rooms. Preferably, the cover 20 is formed of linear, low density polyethylene which is formed into the desired configuration by injection molding. The cover 20 is preferably provided with a wall thickness, except for the latch means 38 and the recess 68, in the range of about 0.010 to 0.060 inch, more preferably about 0.020 to 0.040, and most preferably about 0.030 inch. The outer surface of the tubular portion 22 is preferably provided with a textured surface so as to facilitate the grasping of the cover. This textured surface may be easily provided during the molding or casting of the cover 20.

The handle 14, as best shown in FIGS. 2 and 6–8 and which forms a part of the present invention, has an elongated projection defining a grip portion 72 of a sufficient diameter and length for the convenient grasping thereof. The length of the grip portion 72 from the base 74 to the top 76 of grip portion which is adjacent to the circular shoulder 40 is preferably in the range of about 3 to 5 inches, more preferably about 3.5 inches. The grip portion 72 is of a circular configuration with a tapered cross section increasing in diameter from the base 74 of the handle to the top 76 of the grip portion 72. This tapered cross section normally increases from a diameter in the range of about 0.50 to 1.00 inch at the base 74 to about 0.75 to 1.5 inch at the top 76 of the grip portion 72, more preferably about 0.75 at the base and 1.0 at the top of the grip portion. The angle of the taper provided between the base 74 and the top 76 of the grip portion 72 to the longitudinal axis 37 of the handle is preferably in the range of about 1° to 3° and most preferably about 2°. The tapered grip portion 72 of the handle 14 and the correspondingly tapered tubular portion 22 of the cover 20 facilitates the placement and the removal of the cover 20 onto and from the handle 14, as will be described below. The radially extending circular shoulder 40 on the handle 14 is integral with the grip portion 72 and is attached to the upper body 78 of the handle 14 overlying the grip portion 72. As shown, the shoulder 40 is provided with parallel upper and lower surfaces 80 and 82 that are perpendicular to the longitudinal axis 37 and are interconnected at the radially outermost ends thereof by a rim 84 which is perpendicular to the upper and lower surfaces 80 and 82 of the shoulder 40. The rim 84 and portions of the upper and lower surfaces 80 and 82 contiguous to the rim 84 define lip means which are engaged by the latch means 38 to secure the cover on the handle. If desired, the lower surface 82 of the shoulder 40 may be inclined at an angle generally corresponding to that of the segment 62 of the flange 32 so that when the lip means defined on the shoulder 40 is engaged in the notch 48, the lower surface 82 of the shoulder 40 will bear against the upper surface of the segment 62 over the essentially the entire radial width thereof rather than just at the outermost end surface as would occur with the illustrated embodiment.

Figure 6:
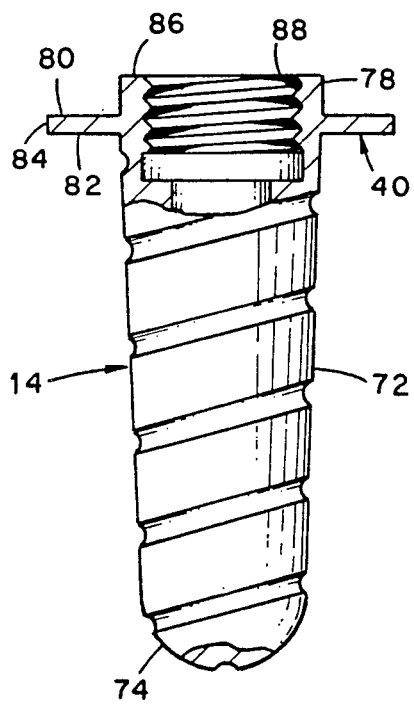
FIG. 6 is a sectional elevational view showing details of one embodiment of the handle of the present invention wherein a threaded receptacle is utilized for attaching the handle to a correspondingly sized and externally threaded boss projecting from the base of a light fixture.

As shown in FIGS. 2 and 6–8, the shoulder 40 is disposed on the upper body 78 of the handle 14 at a location intermediate the grip portion 72 and the top or uppermost end 86 of the handle 14. The spacing between the upper surface 80 of the shoulder 40 and the top end 86 of the handle is sufficient to position the top 86 of the handle 14 in a plane parallel with the rim 36 on the cover 20 as well as maintaining the cavity 34 at an adequate depth so that the latch means 38 can properly function. The handle 14, as shown in the embodiment of FIGS. 2 and 6, is provided with an internally threaded bore 88 in the upper body 78 thereof and in registry with the top 86 of the handle 14. These internal threads extend over a length sufficient to provide adequate structural engagement with an externally threaded boss such as shown at 90 in FIG. 2 extending from the base 15 of the light fixture 10 as well as the positioning of the top 86 of the handle 14 against the base 15 of the light fixture 10.

As described above, the tubular portion 22 of the cover 20 and the grip portion 72 of the handle 14 are provided with tapering cross sections so as to permit the cover 20 to be inserted onto the handle 14 in a manner substantially easier than could be achieved if the walls of the grip portion 72 and the tubular portion 22 were of an uniform or essentially uniform diameter over the length thereof. This tapering of the cover and handle minimizes any build-up of air pressure in the tubular portion 22 during the placement of the cover 20 on the handle 14 as well as minimizing the formation of a vacuum in the tubular portion 22 during the removal of the cover 20 from the handle 14. To further assure that no pressure buildup or vacuum occurs between the cover 20 and the handle 14, a spiral groove as generally shown at 92 may be provided in the surface of the grip portion 72 over essentially the full length thereof. The inner diameter of the tubular portion 22 of the cover 20 is slightly greater than that of the grip portion 72 of the handle 14 so that no expansion of the tubular portion 22 is required for placement of the cover 20 onto the handle 14.

A further feature of the present invention is provided by the shape of the closed end 26 of the cover 20 and the base 74 of the handle 14. As shown, the base 74 of the handle 14 is of a rounded hemispherical or convex configuration to facilitate the reception of the cover 20 onto the handle. This rounded base 74 is, in turn, received in a mating or correspondingly shaped concave receptacle in the end wall 26 of the cover 20.

While only two latches 41 and 42 are shown in FIGS. 2 and 4, it is to be understood that any number of circumferentially spaced apart latches may be readily utilized. For example, four latches may be readily provided with each latch disposed on the flange 32 at locations 90° apart from one another about the circumference of the shoulder 40.

The cover 20, when latched onto the handle 14 as described above, may be readily removed from the handle 14 for disposal or re-sterilization after the use thereof by simply engaging the outer edge of the flange 32 with the fingers of a single hand and then pulling the flange 32 away from the base 15 of the light fixture a sufficient distance to radially displace the latches 41 and 42 away from engagement with the shoulder 40 so that the cover can be slipped off of the handle 14. This simple operation is enhanced by the hinging mechanism provided at the connection of the stepped annular segments 62 and 64 and/or the recess 68.

Figure 7:
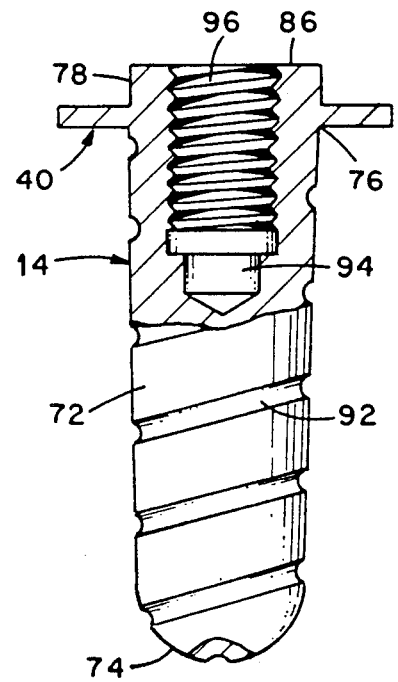
FIG. 7 is a sectional elevational view of a handle similar to the handle depicted in FIG. 6 but differing therefrom by incorporating a longer and narrower threaded receptacle for engaging threads on a longer and thinner threaded boss projecting from the base of a light fixture.
Figure 8:
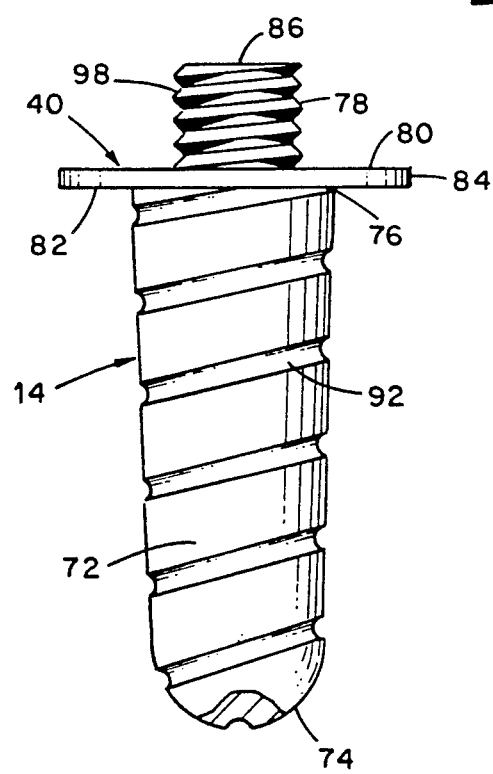
FIG. 8 is a sectional elevational view of a handle similar to the handles depicted in FIGS. 6 and 7 and showing a further embodiment of the handle of the present invention wherein an externally threaded segment at the top end of the handle is utilized for attaching the handle to a threaded socket or receptacle carried by the light fixture.

FIG. 7 shows a further embodiment of the handle 14 wherein a bore 94 extends into the top of handle 14 a sufficient distance to provide an internally threaded receptacle 96 of a greater depth and a narrower diameter than the embodiment shown in FIGS. 2 and 6. FIG. 8 shows a still further embodiment of the handle 14 wherein the upper body 78 of the handle 14 is provided with external threads 98. These external threads 98 are utilized to engage a threaded receptacle (not shown) in the base 15 of the light fixture 10.

In accordance with the present invention the handle 14 may be formed of any suitable material such as metal, wood, or plastic which can be machined, molded, cast, or otherwise formed into the descried handle configuration by following conventional machining and forming practices. Preferably, the handle is formed of a metal such as stainless steel or aluminum which can be readily machined into the desired configuration and which assures that the handle 14 can be readily cleansed of any surface contaminates so as to further assure the integrity of the operating room environment.

In a typical use of the present invention, a lighting fixture 10 in the operating room is first fitted with a handle 14 as described above such as by using a threaded coupling. With the handle 14 so attached, the cover 20 may be readily positioned over the end of the handle 14 and then pushed with a relatively light force onto the handle 14 for urging the latch means 38 out of the way until the shoulder 40 on the handle 14 is receivable in the notches or detents 46 whereupon the latch means rebound or snap back into a latching engagement with the shoulder 40 for securing the cover 20 to the handle 14. The force required for the placement of the cover 20 over the handle 14 is relatively minimal since there is no expansion required of the cover 20 and since the hinge mechanism provides for sufficient radial displacement of the latch mechanisms for engagement with the shoulder 40 when the shoulder 40 becomes aligned with the detents 46.

It will appear clear that the present invention provides a substantially improved cover and handle assembly for use on position-adjustable light fixtures employed in sterile operating room environments such as surgical operating rooms whereby the cover may be readily placed on the handle attached to the light fixtures by the surgeon or any member of the surgical team with minimal exertion and in such a manner that the attachment can be achieved with a single hand and without any contact with the other portions of the light fixture which may introduce contaminates into the operating arena.

What is claimed is:

1. In a lighting fixture which is movable by means of an elongated handle projecting therefrom, the improvement comprising a substantially rigid circumferential shoulder disposed on and extending generally radially from said handle at a location adjacent said fixture, means defining lip means on said shoulder, and cover means for the handle including an elongated tubular portion which is closed at one end and open at its opposite end to define a perimeter, circumferential flange means projecting generally radially outwardly from said perimeter of said open end, latch means carried by said flange means at a location thereon whereby said latch means is in position to engage said lip means when said tubular portion of said cover means is received by said elongated handle and said latch means is urged toward said circumferential shoulder.

2. The improvement of claim 1 wherein said circumferential flange means is resilient so that said latch means can be displaced radially as said cover means is being received on said handle and said latch means is urged into engagement with said lip means and said latch means rebounds to maintain its engagement with said lip means following engagement therewith.

3. The improvement of claim 1 wherein said latch means comprises lug means projecting substantially orthogonally from said flange means on a surface thereof facing said circumferential shoulder on said handle, said lug means including a detent on an end thereof facing said circumferential shoulder, with said detent being of a geometric configuration which permits said detent to engage said lip means.

4. The improvement of claim 1 wherein said lip means is located at the outermost edge of said circumferential shoulder of said handle.

5. The improvement of claim 1 wherein said latch means comprises a plurality of detent means, each of which is disposed at a radial location on that surface of said flange means facing said circumferential shoulder of said handle when said cover is received by said handle such that said latch means will engage said lip means at circumferentially spaced apart locations thereon to secure said cover in position on said handle.

6. The improvement of claim 1 wherein said cover includes hinge means integrally formed with said flange means at least adjacent to said latch means whereby the radial displacement of said latch means as the same is urged into engagement with said lip means is facilitated.

7. The improvement of claim 6 wherein said hinge means comprises a circular reduced wall thickness region that is disposed radially on said flange and said latch means is disposed in said circular region.

8. The improvement of claim 7 wherein said latch means comprises a plurality of projections that are disposed at spaced apart locations along said circular region.

9. The improvement of claim 6 wherein the flange means is of a stepped construction defined by radially spaced circumferential segments having vertically spaced adjacent ends connected by a substantially vertical circumferential segment, wherein the latch means is carried by a radially outermost segment, and wherein said hinge means is provided substantially by the connection between said segments.

10. The improvement of claim 9 wherein said hinge means further comprises a circular reduced wall thickness region in the segment carrying the latch means at a location adjacent to the connection thereof with the vertical segment.

11. The improvement of claim 10 wherein said latch means comprises a plurality of projections that are disposed at spaced apart locations along said circular region.

12. Apparatus for grasping to provide positional movement of a movable lighting fixture comprising handle means including an elongated projection and defining a longitudinal axis, means at one end of the elongated projection for securing said handle to said lighting fixture, circumferential shoulder means extending generally radially outwardly from said elongated projection at a location adjacent to said one end and defining lip means, cover means including an elongated tubular section having a closed end and an open end and being adapted to receive therein a substantial length of said elongated projection of said handle means and further including flange means projecting generally radially from the open end of said elongated tubular portion and having a surface adapted to generally face said circumferential shoulder means when said cover is received by said handle means, and latch means disposed on that surface of said flange means generally facing said circumferential shoulder means at a location thereon which permits said latch means to engage said lip means when said cover is received on said handle means to secure said cover in position on said handle means.

13. The apparatus of claim 12 and including means resiliently mounting said latch means for radial displacement thereof with respect to the longitudinal axis of said handle means when said latch means is engaging and disengaging said lip means.

14. The apparatus of claim 13 wherein said means mounting said latch means comprises hinge means integrally formed with said flange means at a location adjacent to said latch means whereby the radial displacement of said latch means is facilitated.

15. The apparatus of claim 14 wherein said hinge means comprises a circular reduced wall thickness region of said flange means.

16. The apparatus of claim 15 wherein said flange means comprises a stepped construction of radial circumferential segments integrally connected together in said region, and wherein the hinge means further comprises the connection between said segments.

17. The apparatus of claim 13 wherein said latch means comprises a plurality of projections extending from said flange means toward said circumferential shoulder means when said cover is received on said handle, each of said projections including detent means adapted to engage said lip means.

* * * * *